US010200655B2

United States Patent
Kim et al.

(10) Patent No.: US 10,200,655 B2
(45) Date of Patent: Feb. 5, 2019

(54) TOMOGRAPHIC IMAGING METHODS, DEVICES, AND SYSTEMS (71) Applicant: The Trustees of Columbia University in the City of New York, New York, NY (US)

(72) Inventors: Hyun Keol Kim, Cresskill, NJ (US); Andreas H. Hielscher, Brooklyn, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 860 days.

(21) Appl. No.: 14/356,924

(22) PCT Filed: Nov. 8, 2012

(86) PCT No.: PCT/US2012/064163
§ 371 (c)(1),
(2) Date: May 8, 2014

(87) PCT Pub. No.: WO2013/070923
PCT Pub. Date: May 16, 2013

(65) Prior Publication Data
US 2014/0313305 A1 Oct. 23, 2014

Related U.S. Application Data (60) Provisional application No. 61/557,251, filed on Nov. 8, 2011.

(51) Int. Cl.
H04N 7/18 (2006.01)
A61B 5/00 (2006.01)
G06T 7/00 (2017.01)

(52) U.S. Cl.
CPC .......... *H04N 7/18* (2013.01); *A61B 5/0073* (2013.01); *A61B 5/0075* (2013.01); *G06T 7/0012* (2013.01); *A61B 2503/40* (2013.01)

(58) Field of Classification Search
CPC ...... H04N 7/18; A61B 5/0073; A61B 5/0075; A61B 2503/40; G06T 7/0012
(Continued)

(56) References Cited

U.S. PATENT DOCUMENTS 5,070,455 A 12/1991 Singer et al.
8,000,775 B2 8/2011 Pogue et al.
(Continued)

FOREIGN PATENT DOCUMENTS

WO WO 2006/128889 A2 12/2006

OTHER PUBLICATIONS

International Search Report and Written Opinion for International Application No. PCT/US2012/064163.
(Continued)

Primary Examiner — Tung T Vo
Assistant Examiner — Joseph W Becker
(74) Attorney, Agent, or Firm — Potomac Law Group, PLLC; Mark Catan (57) ABSTRACT A multispectral bioluminescence optical tomography algorithm makes use of a partial differential equation (PDE) constrained approach. A sequential quadratic programming (SQP) method is demonstrated that allows for solving both forward and inverse problems at once by updating the forward and inverse variables simultaneously at each step of the optimization iterations. Light propagation in biological tissue is modeled by using the equation of radiative transfer (ERT) and performance of the ERT-based PDE-constrained approach is modeled through numerical and experimental studies.

7 Claims, 5 Drawing Sheets

(58) Field of Classification Search
USPC .......................................................... 348/77
See application file for complete search history.

(56) References Cited

U.S. PATENT DOCUMENTS

| | | | |
|---|---|---|---|
| 8,090,431 B2 | 1/2012 | Wang et al. | |
| 8,676,302 B2 | 3/2014 | Wang et al. | |
| 2003/0011701 A1* | 1/2003 | Nilson | A61B 5/0059 348/370 |
| 2003/0223532 A1 | 12/2003 | Clinthorne et al. | |
| 2004/0039259 A1 | 2/2004 | Krause et al. | |
| 2006/0104536 A1 | 5/2006 | Hsieh et al. | |
| 2007/0244395 A1 | 10/2007 | Wang et al. | |
| 2008/0095422 A1 | 4/2008 | Suri et al. | |
| 2010/0042004 A1 | 2/2010 | Dhawan | |
| 2011/0054298 A1 | 3/2011 | Stamnes et al. | |
| 2011/0142316 A1 | 6/2011 | Wang et al. | |

OTHER PUBLICATIONS

Klose et al., Investigations of RA-Diagnostics applying Optical Tomography in frequency-domain. SPIE vol. 3196, 1998.
Abdoulaev et al., "Optical tomography as a PDE-constrained optimization problem," Inverse Problems, Aug. 23, 2005, vol. 21(5), pp. 1507-1530.
Ahn et al., "Fast iterative image reconstruction methods for fully 3D multispectral bioluminescence tomography," Physics in Medicine and Biology, Jul. 1, 2008, vol. 53(14), pp. 3921-3942.
Alexandrakis et al., "Tomographic bioluminescence imaging by use of a combined optical-PET (OEPT) system: a computer simulation feasibility study," Physics in Medicine and Biology, Sep. 7, 2005, vol. 50(17), pp. 4225-4241.
Ghaudhari et al., "Hyperspectral and multispectral bioluminescence optical tomography for small animal imaging," Physics in Medicine and Biology, Nov. 9, 2005, vol. 50(23), pp. 5421-5441.
Cheong et al., "A review of the optical properties of biological tissues," IEEE Journal of Quantum Electronics, Dec. 1990, vol. 26(12), pp. 2166-2185.
Comsa et al., "Bioluminescence imaging of point sources implanted in small animals post mortem: Evaluation of a method for estimating source strength and depth," Physics in Medicine and Biology, Aug. 21, 2007, vol. 52(17), pp. 5415-5428.
Cong et al., "Practical reconstruction method for bioluminescence tomography," Optics Express, Sep. 5, 2005, vol. 13(18), pp. 6756-6771.
Dehghani et al., "Spectrally resolved bioluminescence optical tomography," Optics Letter, Feb. 1, 2006, vol. 31(3), pp. 365-367.
Dehghani et al., "Spectrally resolved bioluminescence tomography using the reciprocity approach," Medical Physics, Nov. 2008, vol. 35(11), pp. 4863-4871.
Feng et al., "An adaptive regularization parameter choice strategy for multispectral bioluminescence tomography," Medical Physics, Nov. 2011, vol. 38(11), pp. 5933-5944.
Galban et al., "Applications of molecular imaging," Progress in Molecular Biology and Translational Science, 2010 (full date is not available), vol. 95, pp. 237-298.
Gao et al., "Multilevel bioluminescence tomography based on radiative transfer equation Part 1: l1 regularization", Optics Express, Feb. 1, 2010, vol. 18(3), pp. 1854-1871.
Gompels et al., "In vivo optical imaging in arthritis—an enlightening future?," Rheumatology, Mar. 24, 2010, vol. 49(8), pp. 1436-1446.
Gu et al., "Three-dimensional bioluminescence tomography with model-based reconstruction," Optics Express, Aug. 23, 2004, vol. 12(17), pp. 3996-4000.
Han et al., "Bioluminescence tomography with optimized optical parameters," Inverse Problems, May 17, 2007, vol. 23(3), pp. 1215-1228.

Henyey et al., "Diffuse radiation in the galaxy," The Astrophysical Journal, Jan. 1941, vol. 93, pp. 70-83.
Hielscher et al., "Comparison of finite-difference transport and diffusion calculations for photon migration in homogeneous and heterogeneous tissues," Physics in Medicine and Biology, May 1998, vol. 43(5), pp. 1285-1302.
Kim et al., "A PDE-constrained SQP algorithm for optical tomography based on the frequency-domain equation of radiative transfer", Inverse problems, Nov. 24, 2008, vol. 25(1), 015010 (20 pp.).
Kim et al., "Bioluminescence tomography with a PDE-constrained algorithm based on the equation of radiative transfer", Biomedical Optics and 3D Imaging, OSA Technical Digest, Optical Society of America, 2012 (full date is not available), Paper BSu3-89 (3 pp.).
Klose et al., "In vivo bioluminescence tomography with a blocking-off finite-difference SP3 method and MRI/CT co-registration," Medical Physics, Jan. 2010, vol. 37(1), pp. 329-338.
Klose et al., "Optical tomography with the equation of radiative transfer," International Journal of Numerical Methods for Heat & Fluid Flow, May 22, 2008, vol. 18 (3/4), pp. 443-464.
Klose, "Transport-theory-based stochastic image reconstruction of bioluminescent sources," Journal of the Optical Society of America A, Jun. 1, 2007, vol. 24(6), pp. 1601-1608.
Kuo et al., "Three dimensional reconstruction of in vivo bioluminescent sources based on multispectral imaging," Journal of Biomedical Optics, Mar. 1, 2007, vol. 12(2), pp. 24007-1.4007-12.
Lu et al., "Source reconstruction for spectrally-resolved bioluminescence tomography with sparse a priori Information," Optics Express, May 11, 2009, vol. 17(10), pp. 8062-8080.
Lv et al., "Experimental study on bioluminescence tomography with multimodality fusion," International Journal of Biomedical Imaging, Sep. 2007, vol. 2007, Article ID 86741 (4 pages).
Lv et al., "Spectrally resolved bioluminescence tomography with adaptive finite element analysis: methodology and simulation," Physics in Medicine and Biology, Jul. 3, 2007, vol. 52(15), pp. 4497-4512.
Napp et al., "Optical imaging in vivo with a focus on paediatric disease: technical progress, current preclinical and clinical applications and future perspectives," Pediatric Radiology, Feb. 1, 2011, vol. 41(2), pp. 161-175.
Narsinh et al., "Molecular imaging of human embryonic stem cells," Editor: Barry W. Hicks, Viral Applications of Green Fluorescent Protein: Methods and Protocols, Methods in Molecular Biology, 2009 (full date is not available), vol. 515, Chapter 2, pp. 13-32.
Qin et al., "Comparison of permissible source region and multispectral data using efficient bioluminescence tomography method," Journal of Biophotonics, Nov. 2011, vol. 4(11-12), pp. 824-839.
Qin et al., "New optical molecular imaging systems," Current Pharmaceutical Biotechnology, Sep. 1, 2010, vol. 11(6), pp. 620-627.
Saad et al., "GMRES: a generalized minimal residual algorithm for solving nonsymmetric linear systems," SIAM Journal on Scientific and Statistical Computing, Jul. 1986, vol. 7(3), pp. 856-869.
Slavine et al., "Iterative reconstruction method for light emitting sources based on the diffusion equation," Medical Physics, Jan. 1, 2006, vol. 33(1), pp. 61-68.
Wang et al., "Overview of bioluminescence tomography—a new molecular imaging modality," Frontiers in Bioscience, Jan. 1, 2008, vol. 13, pp. 1281-1293.
Wang et al., "In vivo mouse studies with bioluminescence tomography," Optics Express, Aug. 21, 2006, vol. 14(17), pp. 7801-7809.
Zhang et al., "Quantitative bioluminescence tomography guided by diffuse optical tomography," Optics Express, Feb. 4, 2008, vol. 16(3), pp. 1481-1486.
Zhao et al., "Emission spectra of bioluminescent reporters and interaction with mammalian tissue determine the sensitivity of detection in vivo," Journal of Biomedical Optics, Jul. 1, 2005, vol. 10(4), pp. 041210/1-041210/9.

* cited by examiner

TOMOGRAPHIC IMAGING METHODS, DEVICES, AND SYSTEMS

STATEMENT REGARDING FEDERALLY SPONSORED RESEARCH

This invention was made with government support under grant CA126513 awarded by the National Institutes of Health. The government has certain rights in the invention.

BACKGROUND

Radiant source imaging (for example bioluminescence or fluorescence imaging) may be used in in vivo diagnostic studies on animal or human subjects in the areas of medical research, pathology and drug discovery and development, diagnosis, etc. Bioluminescence may be generated by cells that have been transfected with a luminescent label such as luciferase. It may also be used to label molecules of interest. As such it may be used as a marker to indicate a specific tissue type, monitor physiological function, track the movement or distribution of drugs or medicaments, track the distribution of a therapeutic compound administered to the subject, or changes associated with the progression of a disease.

Light from radiant energy sources is strongly scattered in most tissue structures of interest. In addition, tissue structures often contain absorbers. Despite the scattering and absorption, some light can be detected on the surface of a tissue structure. Luminescent imaging systems and methods (e.g., Bioluminescence tomography or "BLT") have been developed that can record the spatial distribution of light emitted from the surface of the subject and used to calculate distribution of sources within the tissue structure.

BLT is an imaging modality that makes use of bioluminescent markers that emit light in response to predefined biochemical environments. The emission of light can be used to detect molecular processes associated with the development of diseases. BLT is used in preclinical experiments using small animals to study various disease processes and drug effects. BLT recovers the spatial distribution of bioluminescence inside the medium from measured intensities on the tissue surface.

Most reconstruction methods developed to date rely on the diffusion approximation (DA) to the equation of radiative transfer (ERT). The DA converts the difficult-to-solve integro-differential ERT into a partial-differential diffusion equation (DE) for which various analytical solution and stable numerical methods exist. The DA is accurate if the absorption coefficient of the medium under consideration is low relative to the scattering coefficient. The approximation becomes less accurate in media with small geometries where boundary effects are dominant, or in fluid-filled, void-like regions. These adverse conditions generally hold in small animal bioluminescence imaging where bioluminescent sources such as luciferases are employed as a light-emitting probe. Such probes have a broad emission spectrum that peaks between 460 nm and 630 nm where intrinsic tissue absorption may be high. Furthermore, the optical path length in small animals, (e.g., mice and rats) is relatively small and boundary effects dominate.

SUMMARY

The disclosed subject matter includes devices, systems and methods adapted for determining and outputting data representing the three-dimensional distribution of light sources inside a structure, such as a mammalian tissue structure. The distribution may characterize the intensity as well as locations of sources. In embodiments, sources emitting light in the near infrared range are used. In embodiments, the tissue structures that are interrogated show a low ratio of absorption to scattering in a substantial part of the wavelength range of the sources.

Known approaches to the inverse bioluminescence problem exploit the linear relationship between bioluminescent sources inside the medium and measurements on the tissue surface. Given a measurement z at the tissue surface, a prediction p is represented by a linear combination representing the unknown source distribution q and its Jacobian matrix (also referred to as a sensitivity matrix) J, which is not a function of q, i.e., p=Jq in a matrix-vector form. The inverse bioluminescence problem reduces to solving the linear equation Jq=z for the unknown vector q, and the inverse solution can be obtained in a least squares sense, i.e., $$\min_q \frac{1}{2} \|Jq - z\|^2,$$

since the number m of measurements available is usually much smaller than the number n of unknown sources to be estimated.

The sensitivity to random noise of linear methods can be mitigated by reformulating the original problem as an approximate problem such as $$\min_q \frac{1}{2} \|Jq - z\|^2 + \beta R(q)$$

where $R(q)$ is a stabilizing term represented by a classical $l_1$ or $l_2$ regularization term with a regularization parameter $\beta$. Nonlinear iterative methods may then be used to solve this regularized minimization problem since $\beta$ is not known a priori and needs to be adjusted iteratively.

Known methods based on the Jacobian matrix require a pre-calculation of the Jacobian coefficients before the reconstruction is started. The Jacobian matrix can be constructed in different ways, for example, the perturbation approach and the adjoint theorem. Given m measurements for n unknowns, the perturbation approach requires n forward runs, while the adjoint theorem only needs m adjoint runs (m<<n). Thus the adjoint theorem is more cost-efficient.

A PDE-constrained multispectral bioluminescence tomography algorithm provides fast image reconstruction while maintaining accuracy. The high speed may be obtained by solving forward and inverse problems simultaneously using a multispectral PDE-constrained optimization approach. A theoretical foundation for the method is described. In addition, details of the forward and inverse solvers are provided and finally results from numerical and experimental phantom examples are described.

Computationally efficient reconstruction methods that allow for fast image reconstruction are highly desirable. In the present disclosure, an approach called PDE-constrained optimization is applied to the nonlinear inverse problem of recovering optical properties of interrogated tissue, such as portions of a living animal. The PDE-constrained approach can lead to a 20-fold speedup in the reconstruction process and is applied to the linearly constrained inverse source problem. This approach is distinct from PDE-constrained methods applied to nonlinear problems and presents different issues in terms of computational efficiency and accuracy.

The disclosed techniques and their associated devices and systems provide the desirable benefits of ERT based image reconstruction for BLT, which include speed. The speed benefits, among other things, permit the computational capacity of a device to be reduced, thereby allowing lower cost devices. They also may enable real time image construction for use in a diagnostic devices, for example. The disclosed methods, devices and systems may be applied for the imaging of target tissues to identify and characterize pathology such as tumors, locate or follow the transport of target compounds such as medicaments or drugs in a host, etc., in large or small animals including humans. The methods devices and systems may be used for other purposes as well.

The disclosed subject matter also includes computer implementable instructions for reconstructing source distribution in a tissue structure. The instructions maybe stored on a medium and implemented on a general purpose computer or an embedded systems attached to a general purpose imaging device such as a camera or a special purpose camera configured with a capability for sensitivity and luminance level resolution in the wavelength range of interest.

Objects and advantages of embodiments of the disclosed subject matter will become apparent from the following description when considered in conjunction with the accompanying drawings.

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

DETAILED DESCRIPTION

Figures 1A, 1B:
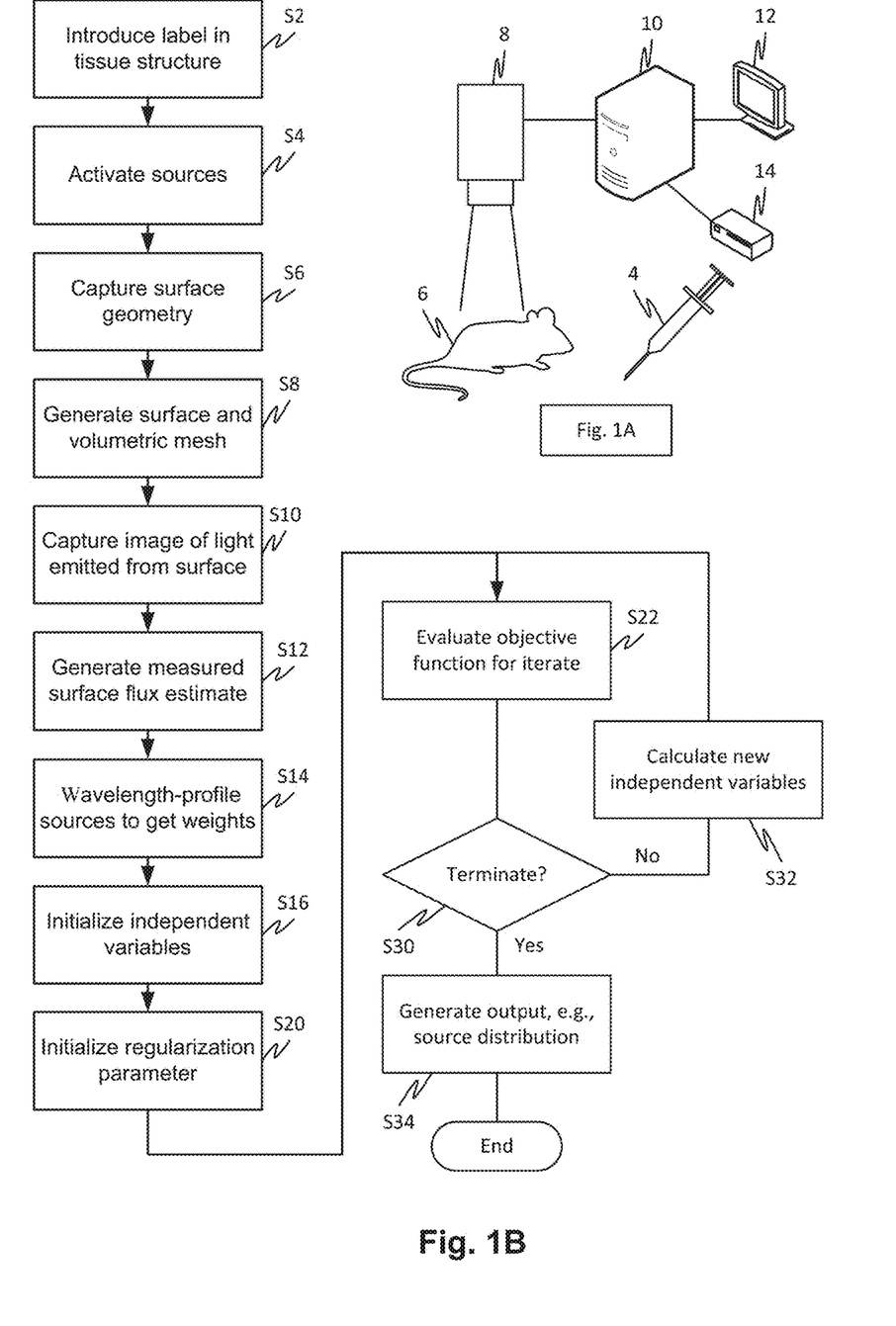
FIG. 1A shows a system arrangement for the capture and development of tomographic data according to an embodiment of the disclosed subject matter.
FIG. 1B shows a method for the capture and development of tomographic data according to an embodiment of the disclosed subject matter.

Referring to FIG. 1A, a general radiation source distribution problem is presented, for example, by injecting a bioluminescent label 4 into a light transmitting (scattering and absorbing) structure such as a tissue structure 6 which maybe, for example, an animal model such as a mouse. The tissue structure may also be other structures such as a body part of a human being or other type of animals, a tissue culture, a three-dimensional engineered tissue culture, a geological structure such as a rock or crystal. The distribution of light on the surface of the tissue structure 6 is captured using a camera 8. In embodiments, a single camera may be moved over multiple positions to capture the light distribution over curved surfaces or multiple cameras may be used for this purpose. Other imaging devices may also be used such as a plenoptic camera, a pinhole camera, or an array of contact or near-contact detectors which detect local light intensity. The light distribution is digitized and stored and processed by a computer 10 for construction of one or more images representing the distribution of light sources within the tissue structure 6. The digitized representation may show the surface intensity distribution for multiple wavelength bands. Labels may also include fluorescent sources (e.g., fluorophores) which emit first radiation in response to second radiation of a different wavelength, usually a longer wavelength.

Referring also to FIG. 1B, as indicated at S2, the tissue structure 6 may be prepared by introducing a label 4 which may attach to predefined types of cells in the tissue structure 6 or which may be attached to a drug, for example. The label 4 may be bioluminescent. The label 4 may be introduced into the circulatory system of the tissue structure 6 and after a time or event, the label may be activated (S4) by the natural environment of the tissue structure 6 or by changing the chemical environment in the tissue structure. At S6, the imaging device 8 may be used to capture the surface geometry of the tissue structure to be used for modeling the internal and surface features thereof. A three-dimensional model and surface and volumetric mesh may be generated from one or more images by the computer 10. To support this process, the camera 8 or tissue structure 6 may be moved in order to capture multiple images at different angular orientations. The pattern of light emitted from the surface of the tissue structure 6 may be captured using the camera 8 as indicated at S10. At S12 the image may be converted into a wavelength frequency and intensity estimate for each surface mesh element by mapping image luminance and chrominance to the surface model.

The surface intensity distribution $z_v$ is the measured parameter that is compared with predictions $p_v$ to optimize the inferred distribution of the scattering and absorbing properties and the distribution of sources (luminescent label) in the volumetric mesh, with the latter distribution being the target data that is output on a display 12 or other output destination such as a data store 14. For example, the source concentration may be rendered as colored transparent contour surfaces of a three-dimensional model of the tissue structure 6. The further operations S14 to S34 are computational processing operations that may be performed by the computer 10 with details of an embodiment described below. At S14, as described with reference to equation 11.1, a combined term for the total energy distribution can be derived by analysis of the source spectrum in order to simplify computation. At S16 and S16, initial values for the independent variables (e.g., source and radiance distribution and Lagrangian multipliers), are stored in a readable data store. At S20, an initial value of a regularization parameter to be used for generating a reduced gradient in the calculation of new iterates is also stored (See eqns. 5 and 7 for example). At S22, a functional that outputs an objective function is calculated based on the current iterate of the independent variables. At S30 a termination condition is tested, for example, a figure of merit is computed for the objective function and compared to a stored condition. If the termination condition is satisfied, an output is generated at S34, for example, a representation of the source distribution. The output may be a real-time display or a stored series of 2D slices or any other suitable data. If the termination condition is not satisfied at S30, then new values of the independent variables are calculated for a new iteration of S22. For example, the Lagrangian multipliers may be computed per eqn. 8 and the source and radiant distributions updated per eqn. 10.

The problem and method of solution presented above presents an example framework for a general approach for solving for the forward and inverse problem that can yield a source distribution inside a structure and thereby be used for research or diagnosis. The following discussion describes background and an efficient method that may be applied by a computation system for providing this source distribution data.

The use of image data may yield large numbers of surface flux measurements which serve as inputs to the source distribution problem identified above. Among known approaches, Jacobian-based approaches may be used, but they tend to be costly with respect to time and memory for large-scale problems where a large number of measurements are used as input to reconstruction, for example in the system of FIG. 1 where a large number of detection points is employed. In such cases, the adjoint theorem may require several hundreds of forward runs just to construct J. For this reason also, commonly employed Jacobian methods may be costly in ERT-based image reconstruction codes, especially because the number of times the ERT is solved increases with the number of detectors.

Conventional Jacobian methods are classified as unconstrained methods in which the inverse variable q is always treated as a function of the forward variable $\psi$, which makes it possible to eliminate the constraint $A\psi=b$ by substituting its solution $\psi=A^{-1}b$ into the objective function $f(q,\psi)$. Then the original constrained problem min $f(q,\psi)$ s.t. $A\psi=b$ is now recast into the unconstrained problem min $f(q,A^{-1}b(q))$, where $f$ is now a function of q only. For the inverse source (e.g., bioluminescence) problem, unconstrained methods of this kind basically require solving the adjoint problem repeatedly up to the number of detectors.

In contrast to Jacobian-based methods, gradient-based techniques used in nonlinear optical tomographic problems can be employed. Among these, quasi-Newton methods build up the approximate Hessian (i.e., $J^TJ$) using only the gradient information through iterations, and in particular their limited-memory version produces the product $(J^TJ+\beta R)^{-1}J^Tz$ directly, thus saving time and memory. However, the quasi-Newton method also requires the complete solution of two equations (the forward and adjoint equations) in order to construct the Hessian matrix or its approximation iteratively, and additional function evaluations are needed as well during line search, which results in a costly process when the ERT is used as a light propagation model.

The following presents the derivation of a disclosed method for estimating the distribution of sources in a medium. Given predictions $p_v$ of measurements $z_v$ at wavelength v made on the tissue structure 6 surface, the multispectral inverse source problem is to find a vector q(r) of spatial bioluminescent sources (e.g., the bioluminescent label) within the tissue structure 6 that minimizes the difference between actual measurements made by detectors, such as the CCD elements of the camera 8, and the predictions as follows:

$$\min_{q,\psi_v} f = \frac{1}{2}\sum_v (Q\psi_v - z_v)^T(Q\psi_v - z_v) + \beta R(q) \quad (1)$$

s.t.

$$C_v = A\psi_v - b_v$$
$$= 0,$$

where $A\psi_v = b_v$ denotes the discretized forward equation and Q denotes the measurement operator that projects the vector of spectral radiances ($\psi$) onto the measurable quantity $p_{v,d} = Q_d \psi_{v,d}$ on the surface of tissue body 6. As suggested by equation (1) all wavelength data can be used simultaneously in the source reconstruction q as discussed below.

The constrained problem (1) is solved directly in the framework of PDE-constrained optimization where the forward and inverse variables are treated independently. The PDE-constrained inverse problem (1) is reformulated into the framework of the following extended objective function called "Lagrangian" as:

$$L(q; \psi_v, \lambda_v) = \frac{1}{2}\sum_v (Q\psi_v - z)^2 + \beta R(q) + \sum_v [\lambda_v^T(A\psi_v - b_v)]. \quad (2)$$

Here $\lambda_v$ is the vector of spectral Lagrange multipliers. The simultaneous solutions of forward and inverse problems can be achieved at points satisfying the first order Karush-Khun-Tucker (KKT) conditions where the gradient of L in (2) vanishes with respect to q, $\psi_v$ and $\lambda_v$, respectively:

$$L_q \equiv \frac{\partial L}{\partial q} = \nabla f_q + \beta \nabla R + \sum_v [(b_v)_q \lambda_v] = 0, \quad (3a)$$

$$L_{\psi_v} \equiv \frac{\partial L}{\partial \psi_v} = \nabla f_{\psi_v} + A^T \lambda_v = 0, \quad (3b)$$

$$L_{\lambda_v} \equiv \frac{\partial L}{\partial \lambda_v} = A\psi_v - b_v = 0, \quad (3c)$$

where the first equation (3a) is the sensitivity equation, the second (3b) and third (3c) equations are the discretized adjoint and forward equations, respectively.

This PDE-constrained approach permits the forward problem solution to be inaccurate during optimization until the optimization reaches convergence. So the inexact solution obtained with a loose criterion can be used in the optimization, which leads to a significant saving in the total reconstruction time. The reduced (or full) Hessian sequential quadratic programming (SQP) method may be used to solve the original multispectral problem (1) by minimizing the multispectral Lagrangian functional (2) with respect to q, $\psi_v$ and $\lambda_v$, respectively. In the following, a description of the reduced Hessian sequential quadratic programming (rSQP) method is provided. Note that for the instant description, the subscript v of all wavelength-dependent variables is omitted for brevity.

Let $x_k=(q,\psi)$ be the current iterate. The rSQP method solves the quadratic approximation of the Lagrangian functional (3) in the reduced space, subject to the linearization of the forward equations, as follows:

$$\text{Min } g_{r,k}^T \Delta q_k = \frac{1}{2}\Delta q^T H_{r,qq} \Delta q_k \qquad (4)$$

subject to $$\frac{\partial C_k}{\partial x}\Delta x_k + C_k = 0$$

where $\Delta x=(\Delta q,\Delta\psi)^T$ is the step for the next iterate, $g_{r,k}$ is the reduced gradient and $H_{r,qq}(q_k)$ is the reduced Hessian of the Lagrangian function. After solving the quadratic problem (4), the following expressions are obtained for the updates $\Delta x=(\Delta q,\Delta\psi)^T$ of the forward and inverse variables:

$$\Delta q_k = -(H_{r,k})^{-1} g_{r,k} \qquad (5)$$

$$\Delta \psi_k = A^{-1}\left(C_k + \frac{\partial C_k}{\partial q}\Delta q_k\right) \qquad (6)$$

where the matrix-vector product $(H_{r,k})^{-1} g_{r,k}$ corresponds to the term $(J^T J)^{-1} J^T z$ in the unconstrained Jacobian method. Quasi-Newton methods may be used to build up the approximate Hessian $H_{r,k}$ (i.e., $J^T J$) iteratively through previous gradient calculations, and in particular the limited memory Broyden-Fletcher-Goldfarb-Shanno (BFGS) updating scheme is employed here to directly produce the product $(H_{r,k})^{-1} g_{r,k}$, to save time and memory. The reduced gradient $g_{r,k}$ is given as:

$$g_{r,k} = \sum_v \left(\frac{\partial b_{v,k}}{\partial q_k}\lambda_{v,k}\right) + \nabla_q f_k + \beta \nabla R \qquad (7)$$

At the new iterate, the Lagrangian multiplier vector is updated as:

$$A^T \lambda_{v,k+1} = -Q^T(Q\psi_{v,k+1} - z_v) \qquad (8)$$

The global convergence of the PDE-constrained multi-spectral algorithm may be ensured by a line search on the following merit function that may balance the aims of reducing the objective function and satisfying the constraints, given as:

$$\varphi(\psi_\lambda, q) = f(\psi_\lambda, q) + \sum_\lambda \eta_\lambda |A\psi_\lambda - b_\lambda|_1. \qquad (9)$$

The function (9) may be chosen for simplicity and low computational cost. The merit function (9) is successively monitored to ensure the global convergence progress towards the optimal forward and inverse solutions, while a line search is performed to find a step length $\alpha^k$ that can provide a sufficient decrease in the merit function. As a consequence, the new iterate is given as:

$$q^{k+1}=q^k+\alpha^k\Delta q^k$$

$$\psi_\lambda^{k+1}=\psi_\lambda^k+\alpha^k\Delta\psi_\lambda^k. \qquad (10)$$

The algorithm as described in equations (1)-(10) was used for the numerical and experimental results presented below.

Light Propagation Model

The forward problem for light propagation in turbid media with a bioluminescent source in each spectral band v can be accurately modeled by the equation of radiative transfer, given by $$(\nabla \cdot \Omega)\psi_v(r, \Omega) + (\mu_a + \mu_s)\psi_v(r, \Omega) = \qquad (11)$$

$$\frac{\mu_s}{4\pi}\int_{4\pi}\psi_v(r, \Omega')p(\Omega', \Omega)d\Omega' + \frac{q_v(r)}{4\pi}$$

where $\psi_v(r,\Omega)$ is the spectral radiation intensity in unit [W/cm$^2$/sr.], $\mu_a$ and $\mu_s$ are the absorption and scattering coefficients, respectively, in units of [cm$^{-1}$], $p(\Omega',\Omega)$ is the Henyey-Greenstein scattering phase function that describes scattering from an incoming direction $\Omega'$ into a scattering direction $\Omega$. The source term $q_v(r)$ is the photon emission in the spectral band v of the total photon emission $$q(r) = \sum_v q_v(r) \qquad (11.1)$$

where $q_v(r)=w_v q(r)$. Each weight $w_v$ can be determined from a spectral analysis over the spectral energy distribution of a bioluminescent source. Thus the total energy distribution $q(r)$ of a bioluminescent source is not a function of wavelength v so data representing an arbitrary number of wavelengths may be used simultaneously in reconstruction as shown below.

To account for the refractive index mismatch at the air-tissue interface, the partially-reflective boundary condition may be represented as:

$$\psi_{v,b}|_{\vec{n}_b\cdot\Omega<0}=R(\Omega',\Omega)\cdot\psi_{v,b}|_{\vec{n}_b\cdot\Omega'>0}, \qquad (12)$$

where $R(\Omega',\Omega)$ is the reflectivity at Fresnel interface from direction $\Omega'$ to direction $\Omega$, $\psi_{v,b}$ is the spectral radiation intensity and subscript b denotes the boundary surface of the medium, while $\vec{n}_b$ is the unit normal vector pointing outwards the boundary surface.

For discretization of (11), an unstructured node-centered finite volume method in the spatial domain and a discrete ordinate method in the angular domain are used. Following unstructured finite-volume discrete-ordinate methods, the discretized form of (11) is obtained by integrating (11) over the control volume and a divergence theorem as:

$$\sum_{j=1}^{N_{surf}} (\vec{n}_j \cdot \Omega^l)\psi_{v,j}^l dA_j + (\mu_a^v + \mu_s^v)\psi_{v,N}^l = \qquad (13)$$

$$\frac{\mu_s^v}{4\pi}\Delta V_N \sum_{l'=1}^{N_\Omega} \psi_{v,N}^{l'} p^{l'l} w^{l'} + \frac{q_v}{4\pi}\Delta V_N$$

where $N_{surf}$ and $N_\Omega$ are the number of surfaces surrounding the node $N(=1, \ldots, N_t)$ and the number of discrete ordinates based on the level symmetric scheme, respectively, $\vec{n}_j$ denotes the surface normal vector, and $\psi_{v,j}^l$ denotes the spectral radiances defined on the j-th surface in direction l. Also the surface intensities $\psi_{v,j}^l$ are related to the nodal intensities $\psi_{v,N}^l$ by the second-order spatial differencing scheme. After discretization of all nodes, the resulting linear equations given by $A\psi_v=b_v$ are solved with a generalized minimum residual (GMRES) Krylov-subspace solver.

Numerical Demonstration

In the following examples, the performance of the disclosed PDE-constrained scheme as applied to the reconstruction of bioluminescent sources inside a medium is demonstrated. A numerical phantom has a circular shape with a diameter of 2 cm, defined by $\Gamma=\{(x, y)|x^2+y^2=1\}$ and one single bioluminescent source with a diameter of 0.2 cm is embedded inside the medium at $\Gamma=\{(x, y)|(x-0.35)^2+(y-0.35)^2=0.2^2\}$. The bioluminescent source has a power density of 1 W/cm$^3$, which is to be found by the PDE-constrained algorithm. For the numerical experiments, spectrally resolved data are considered. The chosen set of three wavelengths is 600 nm, 650 nm and 700 nm, which are linearly independent of and distinguished from each other. The optical properties of the background medium are assumed to be $\mu_a=1.0$ cm$^{-1}$, $\mu'_s=16.7$ cm$^{-1}$ at 600 nm, and $\mu_a=0.5$ cm$^{-1}$, $\mu'_s=15.4$ cm$^{-1}$ at 650 nm and $\mu_a=0.2$ cm$^{-1}$, $\mu'_s=14.3$ cm$^{-1}$ at 700 nm. Seventy-two detector positions are spaced equally around the surface. With this arrangement, three different cases are considered in order to investigate the code performance with respect to CPU times and accuracy, effects of noise and influence of initial guess by comparing the PDE-constrained rSQP scheme and the unconstrained Jacobian scheme.

In the first case, the two methods were compared using the noise-free synthetic data, with a focus on computational efficiency. The noise-free simulated data is obtained by solving the ERT (11) with 24 discrete ordinates for a given set of optical properties. The reconstruction is started from a homogeneous initial guess of the unknown source distribution q, which is set to zero over the entire medium. A $l_2$ regularization operator is employed to eliminate high frequencies components in the reconstructed image, where the regularization parameter β is fixed to a value in the $10^{-3}$-$10^{-6}$ range empirically chosen.

As measures of accuracy, deviation $\delta \in [0,\infty]$ and correlation $\rho \in [-1,1]$ factors were used as given by:

$$\delta = \frac{\sqrt{\sum_{i=1}^{N_t}(q_i^e - q_i^r)^2 N_t}}{\sigma(q^e)}, \quad (14)$$

$$\rho = \frac{\sum_{i=1}^{N_t}(q_i^e - \bar{q}_i^e)(q_i^r - \bar{q}_i^r)}{(N_t - 1)\sigma(q^e)\sigma(q^r)}$$

where $\bar{q}$ and $\sigma(q)$ are the mean value and the standard deviation for the spatial function of the bioluminescent source. Similarly, $q^e$ and $q^r$ are the exact and reconstructed distributions of bioluminescent sources, respectively. Therefore, the smaller δ and the larger ρ, the better image quality. Note that for the measure of δ and ρ only the region of interest (ROI), as defined by $\Gamma_{ROI}=\{(x, y)|(x-0.35)^2+(y-0.35)^2\leq0.4^2\}$ that included a spatial distribution of bioluminescent sources was considered. All reconstructions were performed on an Intel Xeon 3.0 GHz processor.

Figure 2A:
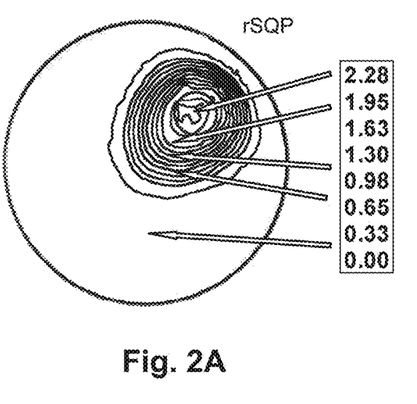
FIGS. 2A and 2B compare spectrally resolved tomographic data using rSQP and Jacobian methods.
Figure 2B:
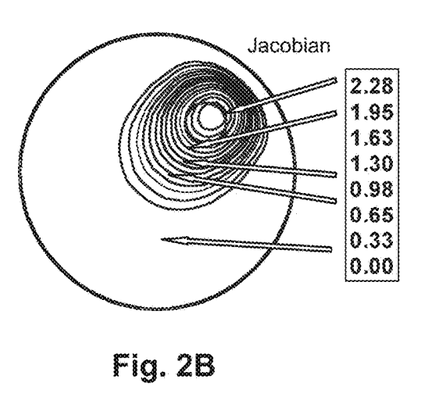

FIGS. 2A and 2B show the reconstruction results of the spectrally resolved data for PDE-constrained rSQP and unconstrained Jacobian methods, respectively. The figures demonstrate that the methods give very similar accuracy: $\rho^{SQP}=0.71$, $\delta^{SQP}=0.92$ and $\rho^{Jacobian}=0.71$, $\delta^{Jacobian}=0.92$ (See equation 14). For the CPU times, however, the PDE-constrained rSQP method converges faster than the unconstrained Jacobian method by a factor of about 14: the rSQP method took only 66 sec to converge, while 907 sec for the Jacobian method. Note that this CPU time (i.e., 66 sec) by the rSQP method is equivalent to the computation effort of less than 6 forward runs, which in turn corresponds to the same computational effort taken to construct the Jacobian matrix for 6 detectors in the Jacobian method.

Figure 3A:
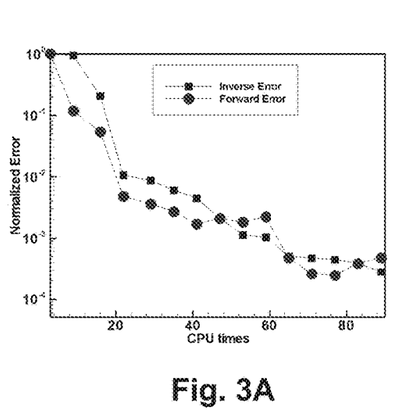
FIGS. 3A and 3B show objective function values of the rSQP and Jacobian methods with respect to iteration numbers and CPU times.
Figure 3B:
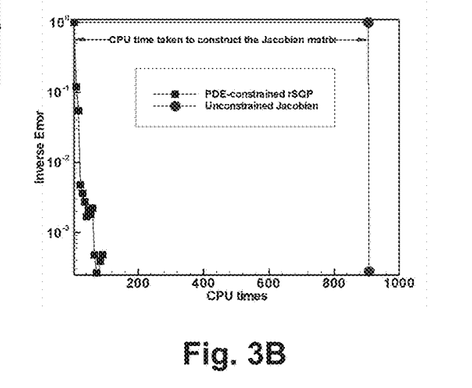

FIGS. 3A and 3B show objective function values of the two methods with respect to iteration numbers and CPU times. This speedup factor can be explained by the fact that since the PDE-constrained rSQP method treats the forward and inverse problems independently, it does not require the complete solution of the forward problem until the final minimum is reached. In other words, the PDE-constrained rSQP algorithm solves the forward equation given by the RTE (11) with a loose tolerance, in the $10^{-2}$-$10^{-3}$ range, during the optimization process, which takes only a fraction of the time required for the exact solution of the forward problem with a tight tolerance FIG. 3 clearly shows this feature of the PDE-constrained rSQP method: both forward and inverse errors decrease in the PDE-constrained rSQP method since it solves both problems simultaneously (FIG. 3a), which leads to the significant difference in the CPU times of the two methods (FIG. 3b).

TABLE 1

Reconstruction quality and computation times with different noise levels.

| SNR | Schemes | CPU time (*) | Cor. ρ | Dev. δ |
|---|---|---|---|---|
| ∞ | PDE-constrained rSQP | 66 s (14) | 0.71 | 0.92 |
|   | Unconstrained Jacobian | 907 s | 0.71 | 0.92 |
| 15 dB | PDE-constrained rSQP | 67 s (14) | 0.74 | 0.90 |
|   | Unconstrained Jacobian | 907 s | 0.72 | 0.93 |
| 10 dB | PDE-constrained rSQP | 79 s (12) | 0.72 | 0.93 |
|   | Unconstrained Jacobian | 920 s | 0.67 | 0.93 |

(*) denotes the acceleration factor by the PDE-constrained method.

Figure 4A:
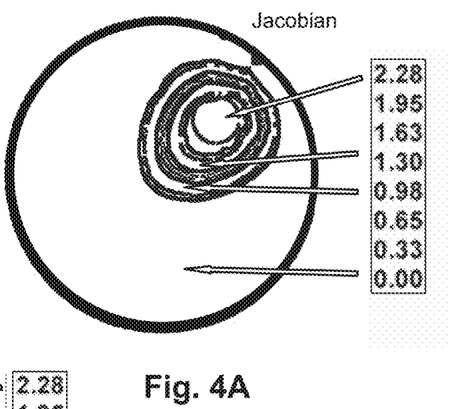
FIGS. 4A and 4B compare reconstructed maps of bioluminescent sources obtained with the PDE-constrained rSQP and unconstrained Jacobian methods for 10 dB noise data.
Figure 4B:
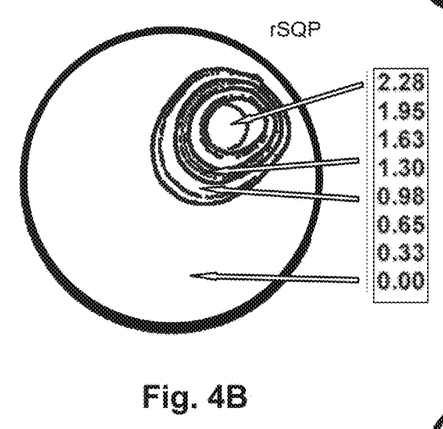

In a second example, the effects of noise on the performance of the two methods is examined. Two different SNR values (15 dB and 10 dB) were used that represent typical noise levels. The CPU time and the deviation $\delta \in [0,\infty]$ and correlation $\rho \in [-1,1]$ factors as given in Table 1. FIG. 4 shows the maps of the reconstructed bioluminescent sources obtained for the 15 dB and 10 dB cases. FIGS. 4A and 4B show reconstructed maps of bioluminescent sources obtained with the PDE-constrained rSQP and unconstrained Jacobian methods, respectively, for the 10 dB noise data.

At noise levels of 10 to 15 dB, the PDE-constrained rSQP method and the unconstrained Jacobian method give somewhat different results; for the 15 dB data $\rho^{SQP}=0.74$, $\delta^{SQP}=0.90$ and $\rho^{Jacobian}=0.72$, $\delta^{Jacobian}=0.93$, and for the 10 dB data, $\rho^{SQP}=0.72$, $\delta^{SQP}=0.93$ and $\rho^{Jacobian}=0.67$, $\delta^{Jacobian}=0.93$. It can thus be said that the PDE-constrained rSQP method is much less influenced by random noise in the measurement than the unconstrained Jacobian method where $\rho^{Jacobian}=0.72$ for 15 dB and $\rho^{Jacobian}=0.67$ for 10 dB. This noise sensitivity of the Jacobian method is related to the direct inversion in $(J^TJ+\beta R)^{-1}J^Tz$ and may be resolved by using the better choice of the regularization parameter in combination to the regularization operator, which is another topic of research on its own, thus being beyond the scope of this work. The fixed regularization parameter $10^{-6}$ was maintained for both methods throughout this work.

TABLE 3

Reconstruction quality and CPU times obtained with the PDE-constrained rSQP scheme for different initial guesses.

| $q^0$ | CPU time (*) | Cor. $\rho$ | Dev. $\delta$ |
|---|---|---|---|
| 1 | 70 s (13) | 0.71 | 0.92 |
| 3 | 65 s (14) | 0.71 | 0.92 |
| 10 | 94 s (9.6) | 0.69 | 0.90 |

(*) denotes the acceleration factor by the pde-constrained method.

For the CPU times, Table 1 shows that the PDE-constrained rSQP method leads to a significant saving in the computation time both for the two noise levels. The PDE-constrained rSQP method took 67 sec while the unconstrained Jacobian method requires 907 sec. The similar reduction is observed for the 10 dB data: the PDE-constrained rSQP method converged after 79 sec while the unconstrained Jacobian method reached convergence after 920 min, which is already a speedup factor of about 12.

In a third case, the influence of initial guess on the algorithm is discussed since gradient-based techniques including the PDE-constrained approach require making an initial guess of the unknowns to start the reconstruction and hence different initial guesses may affect the reconstruction quality. This effect was studied on the PDE-constrained method alone since the Jacobian approach directly solves the linear system and thus is not influenced at all by initial guess. For this study the same setup of the problem was considered as before, and make three different initial guesses ($q^0=1.0$, 3.0 and 10.0) which correspond to 10%, 30%, and 100% respectively, of the actual value of a bioluminescent source. Note that a fixed noise level of 15 dB is used for the reconstructions with three different initial guesses. The reconstruction results and measures of $\delta \in [0,\infty]$ and correlation $\rho \in [-1,1]$ are given in FIGS. 5A and 5B and Table 2, respectively. It can be seen from Table 2 that the PDE-constrained rSQP method leads to similar reconstruction results when the initial guesses are made as 10%, 30% and 100% of the value of the target. For both of the 10% and 30% cases, the same accuracy was observed with $\rho^{SQP}=0.71$ and $\delta^{SQP}=0.92$, and for the 100% case, similar results are obtained with $\rho^{SQP}=0.69$ and $\delta^{SQP}=0.90$, although $\rho^{SQP}$ is slightly decreased. In terms of CPU times, the PDE-constrained code took 70 sec for the 10% case and 65 sec for the 30% case, respectively, which are very similar to the time taken in the previous 15 dB case where the reconstruction is started with zero. Note that the 100% case took a little longer time but this is already expected by the initial guess being too far away from the true solution.

Figure 5A:
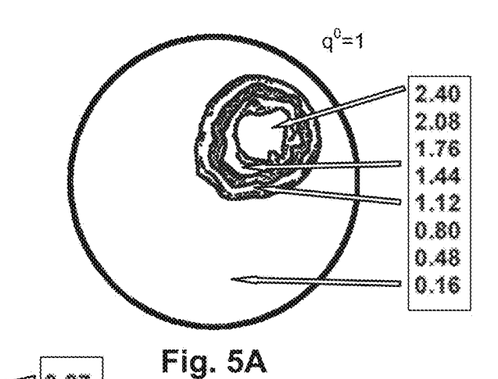
FIGS. 5A and 5B show Reconstructed maps of bioluminescent sources obtained with the PDE-constrained rSQP method for different initial guesses of (a) $q^0=1.0$ and (b) $q^0=10.0$, respectively.
Figure 5B:
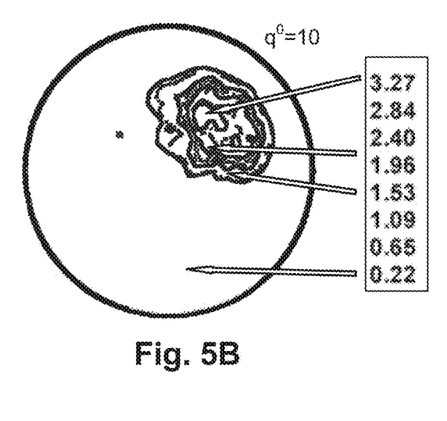

FIGS. 5A and 5B show reconstructed maps of bioluminescent sources obtained with the PDE-constrained rSQP method for initial guesses of (a) $q^0=1.0$ and (b) $q^0=10.0$, respectively. The performance of the presented method using experimental data was also explored. As a light-emitting probe, a quantum dot of 10 nM (Q tracker® 800 Cell Labeling Kit, Invitrogen, cat. no. Q25071MP) was used, which allows for acquisition of spectral emission data over a broad range of wavelengths between 450 nm and 900 nm. With this spectral emission data available, it was sought to find the spatial distribution of the quantum dot as a light-emitting source inside the medium, which is technically equivalent to solving the bioluminescence-enhanced inverse source problem although the quantum dot was used instead of the bioluminescent source.

Figure 6A:
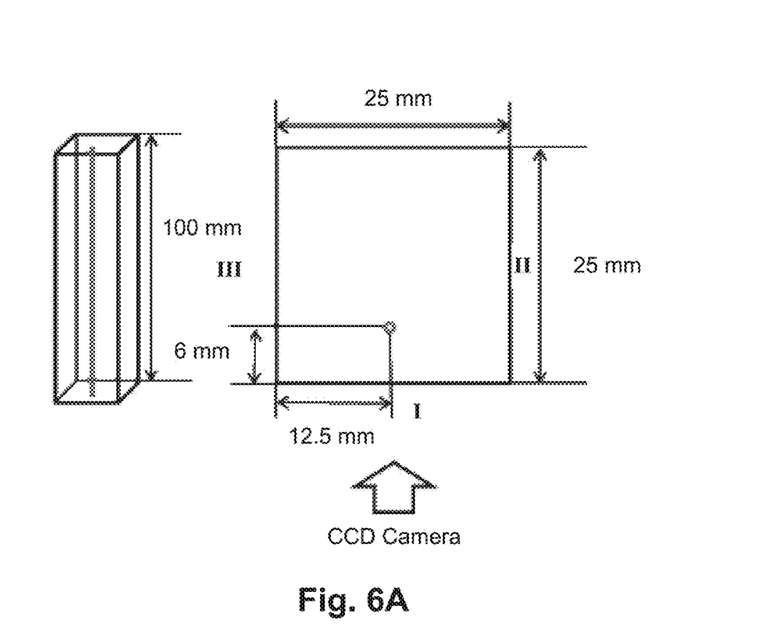
FIG. 6A shows a schematic of the configuration of the phantom used and the position of the CCD image for phantom demonstration tests.
Figure 6B:
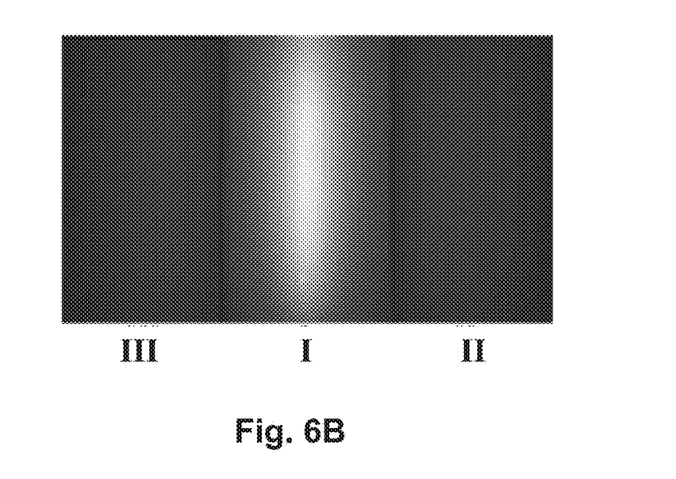
FIG. 6B shows a CCD camera image taken for the three sides (I, II, III) of the phantom for the wavelength of 800 nm for phantom demonstration tests.

FIGS. 6A and 6B show a schematic of the phantom used (left and middle) and the CCD image (right) taken for the three sides (I, II, III) of the phantom for the wavelength of 800 nm. As shown in FIG. 6A, the square cylinder has a size of 25 mm×25 mm×100 mm (X×Y×Z) and is filled with 10% Intralipid fluid of known optical properties for all wavelengths considered here. A smaller cylinder rod with a diameter of 1.5 mm is filled with the quantum dot and embedded inside the background medium. Excitation of the quantum dot and measurement of spectral intensities were made with the Maestro 2 In Vivo Imaging system (CRI Inc., Woburn, Mass.): a 455 nm (±20 nm) excitation filter set was used and the emission was measured with a 700 nm long pass filter and a liquid crystal tunable filter (LCTF) with a 10 nm bandwidth step from 700 nm to 900 nm.

Figure 7A:
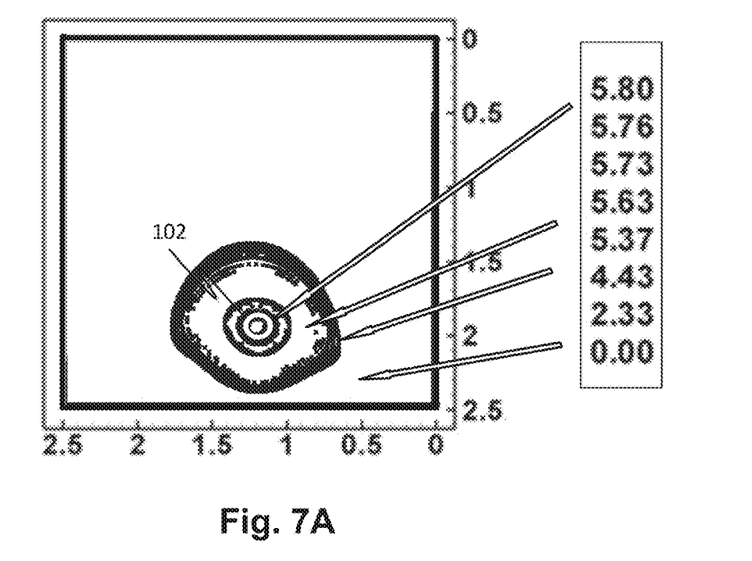
FIGS. 7A and 7B show reconstructed maps of a quantum dot inside an experimental phantom obtained with the spectrally resolved data (710, 730, 750 nm) highlighting the location of a cylinder rod (102) filled with a quantum dot using PDE constrained rSQP and unconstrained Jacobian approaches, respectively.
Figure 7B:
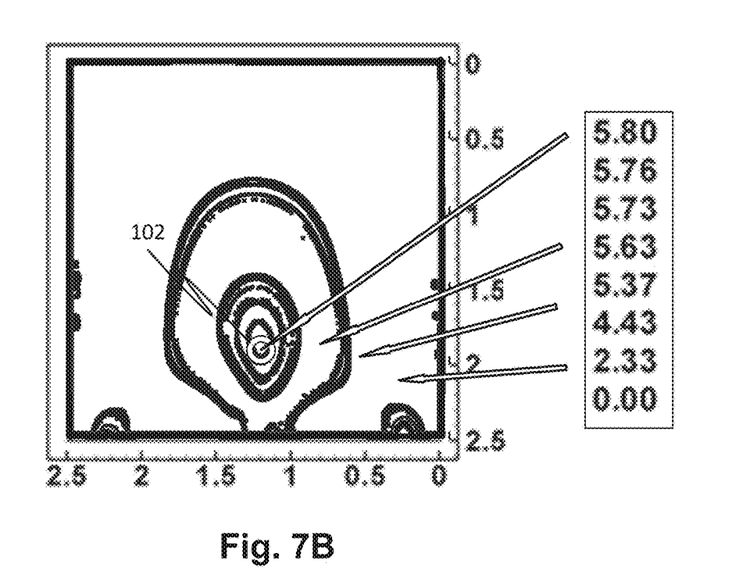

FIGS. 7A and 7B shows reconstructed maps of a quantum dot inside the experimental phantom obtained with the spectrally resolved data (710, 730, 750 nm). The hollow circle 102 indicates the location of the cylinder rod filled with a quantum dot. As shown in FIGS. 7A and 7B, three sides (I, II and III) of the phantom were imaged onto one CCD image: side I was directly imaged to the CCD, and sides II and III were first redirected with a 45° mirror and imaged onto the CCD camera. On the CCD image the 2×2 binning was used that yields an image scale at which 1 pixel equals 0.167 mm. Since the exact strength of a source is not known a priori, the normalized data was used for reconstruction. Data were obtained for three spectral bands (710 nm, 730 nm, 750 nm), which is chosen to match the actual spectral bands of luciferase enzymes, and for each spectral band 41 points were taken from each side, which yields a data set of total 123 points for reconstruction.

The reconstruction of the quantum dot inside the medium was carried out for a two-dimensional plane. The 2D square domain is covered with a structured mesh of 5200 triangles, and 24 discrete ordinates were used to discretize the radiative transfer equation in the angular domain. The reconstruction started from an initial guess $q^0=0$. FIGS. 7A and 7B show the reconstruction results of the spatial distribution of a quantum dot inside the lab phantom obtained by the two methods. Note that the images are displayed in arbitrary unit [a.u.] since the strength of a source is not known. The hollow circle 102 represents the actual location of the quantum dot embedded inside the medium.

The results show that the PDE-constrained rSQP method gives very accurate localization and identification of the quantum dot while the unconstrained Jacobian method seems to retrieve the quantum dot well but produces more artifacts mainly due to random noise in the measurement, which also agrees with the numerical results. The CPU times taken for the two methods was also measured. As expected, the unconstrained Jacobian method needed a total computation effort of about 2230 sec taken for a pre-calculation of the Jacobian matrix using 123 forward runs, whereas the PDE-constrained method took only 103 sec to converge, which yields an 22 fold speedup.

A PDE-constrained reduced Hessian sequential quadratic programming (rSQP) method solves the bioluminescence inverse source problem in a computationally efficient manner. The disclosed algorithm embodiments solve the forward and inverse problems simultaneously by treating the forward and inverse variables independently, which consequently leads to a significant time saving in the reconstruction process. Numerical experiments and experimental studies show that the disclosed PDE-constrained rSQP methods increases the reconstruction speed by a factor of 14 to 22 as compared to the unconstrained Jacobian method that is believed to be the most widely used unconstrained method. Both methods show similar accuracy for all tested cases with respect to effects of noise and initial guess.

The algorithm presented here may accelerate the reconstruction of sources in combination with any forward model. The advantages will be greatest for small geometries typical for small-animal imaging that requires the RTE as a forward model.

Given measurements $z_d$ of outgoing radiances at multiple locations d on the surface of an object, the disclosed method finds a distribution of light-emitting sources q inside the medium that leads to measurements $z_d$ on the surface. According to the method, an initial assumption of radiance $\psi$ and the source quantity q for each mesh element is made. Predictions $p_d = Q\psi$ are computed at locations d for which measurements $z_d$ are available and the current set of radiance $\psi$ and source q satisfies the forward error given by $A\psi - b$ and at the same time the inverse error given by $$\frac{1}{2}\sum_d (p_d - z_d)^2.$$

The algorithm iterates until these conditions are met. If not, the next iterate is determined, the iterate being a new radiance $\psi$ and source q for each mesh element. The change in source q is obtained from equation (5) and the change in radiance $\psi$ from equation (6) to get the changes $\Delta q$ and $\Delta\psi$, in q and $\psi$, respectively. These are used to obtain the next iterate: $q^{new} = q + \Delta q$ and $\psi^{new} = \psi + \Delta\psi$. At each iteration, the two equations, (5) and (6) are calculated. Thus, according to this method, the two errors (forward and inverse errors) are minimized simultaneously through the successive iterations. This is provided through minimizing the extended objective function where the Lagrange multiplier generally causes the updates in q which improve the estimation of $\psi$. Thus, the Lagrange multiplier facilitates the simultaneous minimization of the forward and inverse errors.

According to embodiments, a system for estimating a distribution of radiative sources in a scattering medium has a programmable controller with a data store and an output port and any other digital resources required for implementing a method. An imaging device may be connected as part of the system or the system may include only a processor with an input port for an image process and software for implementing the following method. The method includes receiving data representing images captured by said imaging device. The images show the surface of an object to allow light emitted from the surface to be transformed into surface flux estimates applied to a model for optimizing a model of the source distribution enclosed by the surface (the scattering medium being enclosed). A data store may be used to contain a computer readable program for implementing the method. The program may include steps that control the imaging device to capture light leaving the surface of the object and to store image data representing said light leaving said surface. The stored program may also include a mesh generator. The mesh generator may produce an unstructured mesh based on a model of the tissue structure within the enclosing surface. The method may include generating a mesh and determining light leaving the enclosing surface for each mesh element defining a portion of the enclosing surface. This may be derived from the image data using techniques that are known, such as planar projection and scaling.

The method includes executing an iterative minimization algorithm to estimate the distribution of the sources; and outputting data representing the distribution. The estimating may include iteratively calculating an objective function that measures an error in a source distribution within an optical medium, the objective function representing a difference between predicted and measured values of the light output at the plurality of detection positions and a constraint representing the radiative transfer in the scattering medium. The method may include evaluating the properties of an objective function by solving the objective function at multiple combinations of independent variables, a first of said independent variables corresponding to the distribution of the sources and a second of said independent variables corresponding to the vector of radiances. The updating may be effective, over successive iterations, to converge on a minimum of said objective function.

The multiple combinations of independent variables include a vector Lagrangian multipliers. The objective function may include a regularization function that stabilizes the inversion process. The plurality of detection positions may be greater than 100. In further embodiments, the detection positions may number in the thousands. The objective function may include a parameter representing a weighted sum of the spectral components of the sources. The weighted sum may be based on measured emission data from sample sources. The imaging device may include a CCD camera. A display may be provided and the method may include generating a real time display that includes the generation of an image sequence showing data responsive to said source distribution over time.

According to embodiments, the disclosed subject matter includes a method for generating tomographic data. The method includes generating light from a distribution of sources within a light-scattering medium, wherein the distribution of sources may be unknown. The method further includes detecting light output at a plurality of detection positions on a surface of the scattering medium. The method further includes estimating the distribution of the sources, including position and density thereof, within the medium using an iterative non-linear solver to minimize an objective function depending on independent variables including a forward variable representing radiance, and an inverse variable representing source distribution, the independent variables being varied independently in successive iterations of the non-linear solver. The forward variable may be solved iteratively until a convergence criterion may be met. The plurality of detection points may be more than 100 or more than 1000 detection points. The objective function may provide a measure of the closeness of a fit between measured values of the light output at the plurality of detection positions and predictions of the light output based on a current iteration's representation of the source distribution with a constraint that depends on the radiance. The constraint may depend on the radiance may be a linear estimation based on the equation of radiative transfer. The medium may be a living tissue or any other structure that scatters light from sources embedded therein.

The living tissue may be of a mammal or small animal such as a laboratory mouse or rat. The living tissue may also be a human body part. The sources may be bioluminescent labels, i.e., molecules with a binding affinity for cells or proteins whose location or transport is to be studied. In embodiments, bioluminescent labels are transfected to cells.

The iterative non-linear solver may minimize an extended objective function whose gradient depends on a current iterate of source distribution, radiance, and Lagrange multipliers. The minimizing of the objective function may be such that the independent variables converge simultaneously in the successive iterations.

The independent variables may include Lagrangian multipliers derived from a corresponding constrained optimization problem in which the objective function quantifies a difference between predicted and measured values of the light output at the plurality of detection positions and a constraint representing the radiative transfer in the scattering medium.

According to embodiments, the disclosed subject matter includes a method for generating tomographic data. The method includes generating light from a distribution of sources within a light-scattering medium, wherein the distribution of sources may be unknown. The method further includes detecting light output at a plurality of detection positions on a surface of the scattering medium. The method further includes estimating the distribution of the sources and outputting data representing the distribution. The estimating includes iteratively evaluating the properties of an objective function by solving the objective function at multiple points and iteratively converging on a minimum of said objective function, wherein the objective function represents a difference between predicted and measured values of the light output at the plurality of detection positions and a constraint representing the radiative transfer in the scattering medium.

The method may further include receiving the data output in the outputting and generating a visual representation of the estimated source distribution. The visual representation may include an image sequence representing changes in said source distribution over time. The plurality of detection points may be more than 1000 detection points. The medium may be a living tissue. The living tissue may be of a animal such as a mammal. The sources may be bioluminescent labels. The bioluminescent labels may be transfected to cells. The objective function may be characterized by a gradient that depends on source distribution, radiance, and Lagrange multipliers. The objective function may depend on a regularization parameter that penalizes complexity in the objective function. The method may include capturing a surface model of said scattering medium and generating a surface and volume mesh of said scattering medium. The estimating may be responsive to said surface model and said volume mesh. The detecting light output may include imaging the surface of the scattering medium with a CCD optical imaging device. The method may further include mapping signals from the CCD optical imaging devices to estimates of flux leaving respective portions of said volume mesh. The mapping may include calculating reflection at said surface. The mapping may include transforming luminance received at respective pixels into an estimate of flux through a surface of said scattering medium.

According to embodiments, the disclosed subject matter includes a system for generating tomographic data. In the system, a programmable controller with a data store and an output port is connected to control an imaging device to apply data representing images captured by said imaging device. A data store contain a computer readable program for implementing a method for controlling the imaging device to capture light leaving a surface of a scattering body and for storing image data representing said light leaving said surface. The stored method includes generating a mesh and determining light detecting light output at a plurality of detection positions on a surface of the scattering medium. The method further includes executing an iterative minimization algorithm to estimate the distribution of the sources and outputting data representing the distribution. The data may be stored or rendered on a display as a static or moving image. The data may be represented in any form suitable for the display of three-dimensional data. The estimating may include iteratively evaluating the properties of an objective function by solving the objective function at multiple points and iteratively converging on a minimum of said objective function, wherein the objective function represents a difference between predicted and measured values of the light output at the plurality of detection positions and a constraint representing the radiative transfer in the scattering medium.

The method further may include receiving the data output in the outputting and generating a visual representation of the estimated source distribution. The visual representation may include an image sequence representing changes in said source distribution over time. The plurality of detection points may be more than 1000 detection points. The medium may be a living tissue. The living tissue may be of a mammal. The sources may be bioluminescent labels. The bioluminescent labels are transfected to cells. The objective function may be characterized by a gradient that depends on source distribution, radiance, and Lagrange multipliers. The objective function may depend on a regularization parameter that stabilizes the inversion process.

According to embodiments, the disclosed subject matter includes a method for detecting a distribution of radiation sources inside an object. The method includes capturing image data responsively to radiation emitted from a surface of the object and converting the image data to radiation flux data representing radiation emitted at predefined portions of said surface, the converting including compensating for refractive index mismatch at the surface. The method includes storing medium data representing a predicted distribution of radiation scattering properties inside the object. The method also includes iteratively solving for a source distribution of said radiation sources that predicts the radiation emitted at the predefined portions, the solving including searching for an extremum of a multispectral Lagrangian functional representation of the independent source distribution and spectral radiance distribution and outputting data representing a source distribution resulting from said iteratively solving.

The method may further include storing source data representing an initial estimate of a distribution of radiation sources within said object, said iteratively solving being responsive to said initial estimate. The method may further include storing flux data representing an initial estimate of a distribution of radiation within said object, said iteratively solving being responsive to said initial estimate. The iteratively solving may be effective to converge spectral radiance distribution and source distribution simultaneously such that the spectral radiance distribution may be solved with a progressively smaller tolerance as the iteratively solving approaches the extremum. The Lagrangian functional may be derived from a Lagrangian formulation of a constrained optimization employing the Lagrangian multiplier method of finding an extremum of an objective function (a misfit between predictions and measurements) subject to a linear constraint (discretized formulation of the radiation transfer equation). The method may further include storing at least one emission parameter responsive to a sum-product over a substantial portion of range of wavelengths of the radiation emitted by said sources, said iteratively solving being responsive to said at least one emission parameter. The sources may be bioluminescent sources. The iteratively solving may account for reflection of radiation at said surface.

It will be appreciated that the modules, processes, systems, and sections described above can be implemented in hardware, hardware programmed by software, software instruction stored on a non-transitory computer readable medium or a combination of the above. For example, a method for generating tomographic data can be implemented, for example, using a processor configured to execute a sequence of programmed instructions stored on a non-transitory computer readable medium. For example, the processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system. Exemplary structural embodiment alternatives suitable for implementing the modules, sections, systems, means, or processes described herein are provided below.

The modules, processors or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their sub-components or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer readable medium).

Furthermore, embodiments of the disclosed method, system, and computer program product may be readily implemented, fully or partially, in software using, for example, object or object-oriented software development environments that provide portable source code that can be used on a variety of computer platforms. Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the method, system, and computer program product can be implemented in hardware and/or software using any known or later developed systems or structures, devices and/or software by those of ordinary skill in the applicable art from the function description provided herein and with a general basic knowledge of optical tomography, optimization methods, and/or computer programming arts.

Moreover, embodiments of the disclosed method, system, and computer program product can be implemented in software executed on a programmed general purpose computer, a special purpose computer, a microprocessor, or the like.

It is, thus, apparent that there is provided, in accordance with the present disclosure, optical tomographic methods, devices and systems. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicants intend to embrace all such alternatives, modifications, equivalents, and variations that are within the spirit and scope of the present invention.

What is claimed is:

1. A system for generating tomographic data, comprising:
a programmable controller with a data store and an output port;
an imaging device configured to capture light originating from one or more sources of light disposed within a scattering body and connected to said programmable controller to output data representing images captured by said imaging device;
the data store containing a computer readable program for implementing a method for controlling the imaging device to capture light leaving a surface of the scattering body and for storing image data representing said light leaving said surface;
the method including generating a mesh and determining light output at a plurality of detection positions on a surface of the scattering body without an external light source;
the method including executing an iterative minimization algorithm to estimate a distribution of the one or more sources of light disposed within the scattering body; and
outputting data representing the estimated distribution of the one or more sources of light disposed within the scattering body, wherein
the estimating includes iteratively evaluating properties of an objective function by solving the objective function at multiple points and iteratively converging on a minimum of said objective function, wherein the objective function represents a difference between predicted and measured values of the light originating from the one or more sources of light disposed within the scattering body and output at the plurality of detection positions and a constraint representing a radiative transfer in the scattering body, wherein the objective function is characterized by a gradient that depends on source distribution, radiance, and Lagrange multipliers, and wherein the scattering body is a living tissue of a mammal.

2. The system of claim 1, wherein the method further includes receiving the data output in the outputting and generating a visual representation of the estimated source distribution.

3. The system of claim 2, wherein the visual representation includes an image sequence representing changes in said source distribution over time.

4. The system of claim 1, wherein the plurality of detection positions is more than 1000 detection positions.

5. The system of claim 1, wherein the sources are bioluminescent labels.

6. The system of claim 5, wherein the bioluminescent labels are transfected to cells.

7. The system of claim 1, wherein the objective function depends on a regularization parameter that penalizes complexity in the objective function.

* * * * *